United States Patent
Bonelli et al.

(10) Patent No.: US 11,903,800 B2
(45) Date of Patent: *Feb. 20, 2024

(54) TRANSVERSELY EXTENSIBLE CONTINUOUS ELASTIC LAMINATE, AND A METHOD FOR PRODUCING THE SAME

(71) Applicant: Fameccanica.Data S.p.A., San Giovanni Teatino (IT)

(72) Inventors: Guido Bonelli, San Giovanni Teatino (IT); Gabriele Sablone, San Giovanni Teatino (IT)

(73) Assignee: Fameccanica.Data S.p.A. (IT)

( * ) Notice: Subject to any disclaimer, the term of this patent is extended or adjusted under 35 U.S.C. 154(b) by 0 days.

This patent is subject to a terminal disclaimer.

(21) Appl. No.: 17/675,306

(22) Filed: Feb. 18, 2022

(65) Prior Publication Data
US 2022/0265482 A1 Aug. 25, 2022

(30) Foreign Application Priority Data
Feb. 22, 2021 (EP) .................................... 21158348

(51) Int. Cl.
*A61F 13/15* (2006.01)
*A61F 13/49* (2006.01)
*B32B 37/14* (2006.01)
*B32B 5/04* (2006.01)
(Continued)

(52) U.S. Cl.
CPC .. *A61F 13/15593* (2013.01); *A61F 13/15699* (2013.01); *A61F 13/4902* (2013.01); *B32B 5/04* (2013.01); *B32B 7/05* (2019.01); *B32B 37/14* (2013.01); *B32B 38/0004* (2013.01); *B32B 38/1875* (2013.01); *A61F 2013/49033* (2013.01); *B32B 2307/51* (2013.01); *B32B 2555/02* (2013.01)

(58) Field of Classification Search
CPC .......... A61F 13/15577; A61F 13/15593; A61F 13/153699; A61F 13/15739; A61F 13/15756; A61F 13/15764; A61F 13/4902; A61F 2013/15861; A61F 2013/49033; B32B 38/0004; B32B 38/1875; B32B 2307/51; B32B 2555/02
See application file for complete search history.

(56) References Cited

U.S. PATENT DOCUMENTS

| 2005/0215963 | A1* | 9/2005 | Autran | A61F 13/49015 604/385.27 |
| 2017/0252229 | A1* | 9/2017 | Bonelli | A61F 13/49014 |
| 2022/0265481 | A1* | 8/2022 | Bonelli | B32B 38/0004 |

FOREIGN PATENT DOCUMENTS

EP 3213728 A1 9/2017

OTHER PUBLICATIONS

European Search Report dated Aug. 16, 2021. 5 pages.

* cited by examiner

*Primary Examiner* — Humera N. Sheikh
*Assistant Examiner* — Kevin Ct Li
(74) *Attorney, Agent, or Firm* — RMCK Law Group PLC

(57) ABSTRACT

A transversally extensible elastic laminate including two continuous tab chains having respective continuous base portions sandwiched between two corresponding edge portions of two overlapped webs and a plurality of tabs extending from the respective base portions outside the two overlapped webs, wherein each tab has a respective micro-hook pad fixed to a planar surface, and wherein the planar surface of each tab has a portion which completely surrounds the respective micro-hook pad.

14 Claims, 4 Drawing Sheets

(51) Int. Cl.
*B32B 7/05* (2019.01)
*B32B 38/00* (2006.01)

TRANSVERSELY EXTENSIBLE CONTINUOUS ELASTIC LAMINATE, AND A METHOD FOR PRODUCING THE SAME

CROSS-REFERENCE TO RELATED APPLICATION

This application claims priority to European Patent Application No. 21158348.9 filed Feb. 22, 2021. The disclosure of the above application is incorporated herein by reference in its entirety.

FIELD OF THE INVENTION

The present invention relates to a transversely extensible continuous elastic laminate.

The present invention has been developed with particular reference to the production of disposable absorbent sanitary articles, such as, for example, diapers, training pants, absorbent sanitary products for incontinent adults, etc.

A transversely extensible continuous elastic laminate may constitute a semi-finished intermediate product which can be used for supplying machines for manufacturing absorbent sanitary articles. The transversely extensible continuous elastic laminate can be cut transversely to produce elastic side panels for absorbent sanitary articles. Discrete left and right fastening tabs could be already attached externally on the elastic laminate.

Embodiments of the present invention also relate to elastic side panels for absorbent sanitary articles.

The present invention also relates to a method for producing a transversely extensible continuous elastic laminate.

PRIOR ART

An absorbent sanitary article wearable as a pant typically has a structure that comprises a rectangular-shaped central body or chassis and at least one pair of side panels which extend laterally from opposite sides of the central body in the front or rear section of the central body. The side panels are provided with fastening tabs, typically comprising micro-hooks pads, which can be releasably attached to a web for closing the absorbent sanitary article around the waist of the user. The side panels of an absorbent sanitary article are usually elastically extensible.

Elastic side panels, due to the function that they perform—namely to maintain the absorbent article closed around the waist of the user—are subject to high stresses which can easily lead to breaking the joint between the elastic portions of the side panels and the fastening tabs carrying the micro-hooks pads.

EP-A-3213728 discloses a transversely extensible elastic laminate comprising: a first and a second web, having respective pleated central portions, an elastic tape sandwiched between the pleated central portions of the first and second web and elastically stretchable in a transverse direction, and a plurality of fastening tabs spaced apart from each other in a longitudinal direction. The fastening tabs each include a rectangular support web and a micro-hook pad fixed at a distal end of the rectangular support web.

A first drawback of this prior art solution is that the fastening tabs are connected to the first and second web along a relatively small area. When the user pulls the fastening tab, the stress is distributed only to a limited area of the elastic portion of the side panel, which increases the risk of breaks.

A second drawback of this known solution is that the micro-hook fastening pads extend for the whole width of the support tape, i.e., the lateral edges of the micro-hook pads are aligned to the lateral edges of the support web. When touching the fastening tab, the user perceives a sharp feeling due to the fact that the rigid micro-hook pads extend up to the edges of the fastening tab. This structure of the fastening tabs gives rise to an unpleasant stiffness and sharpness perception during the application of the sanitary article to the wearer. It is not unusual that the user gets scratches or small cuts on the soft skin under the nails due to the contact with sharp and rigid edges of the micro-hook pads.

Regarding the manufacturing method, in the prior art the fastening tabs are supplied as discrete elements set at a constant pitch, which requires complex and expensive apparatuses.

OBJECT AND SUMMARY OF THE INVENTION

The object of the present invention is to overcome the drawbacks of the prior art outlined above.

According to a first aspect of the invention, this object is achieved by a transversely extensible continuous laminate having the features of claim 1.

The transversely extensible continuous laminate can be collected in reels which can be used for supplying machines for manufacturing absorbent sanitary articles. The fact that the transversely extensible laminates for producing the elastic side panels are supplied to the manufacturing machines in a ready-to-use form simplifies considerably the manufacturing machines, which do not need to include all the apparatus, devices and components necessary for the in-line manufacturing of the elastic side panels, which are a substantial part of the machines for manufacturing absorbent sanitary products. This also involves substantial energy savings, which have a positive impact on the sustainability of the manufacturing process.

According to another aspect, the present invention relates to an elastic side panel for absorbent sanitary articles having the features of claim 6.

According to another aspect, the invention relates to a method for producing a transversely extensible laminate having the features of claim 10.

The manufacturing method as compared to the prior art provides a better control on the distance between the fastening tabs, which in the method according to the invention are not applied as discontinuous discrete elements. This reduces manufacturing wastes and has a direct positive impact on the sustainability.

The claims form an integral part of the technical disclosure provided here in relation to the invention.

BRIEF DESCRIPTION OF THE DRAWINGS

The present invention will now be described with reference to the attached drawings, provided purely by way of non-limiting example, wherein.

In the following description, identical or similar components will be indicated by the same reference numerals.

It should be appreciated that the attached drawings are schematic and not to scale with respect to real products. Various figures may not be represented in the same scale. Also, in various figures some elements may not be shown to better show other elements.

DETAILED DESCRIPTION

FIGS. 1-3 and 4-9 schematically show various steps for producing a transversely extensible continuous elastic laminate.

Figure 1:
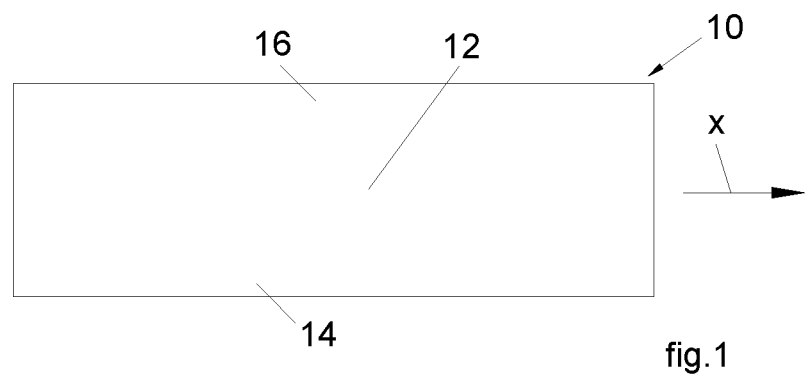
FIGS. 1-3 and 5-9 are schematic plan views showing various steps of a method for producing a transversely extensible continuous elastic laminate having integrated micro-hook fastening elements.

In a first step, shown in FIG. 1, a first continuous web 10 is fed in a longitudinal direction X. The first continuous web 10 may be made of a non-woven material and may be unwound from a reel. The first continuous webs 10 has a central portion 12 and first and second edge portions 14, 16 opposite to each other with respect to the central portion 12.

The first continuous web 10 may be positioned on the outer surface of a wheel or on the upper surface of a conveyor belt as it advances continuously in the longitudinal direction X.

Figure 2:
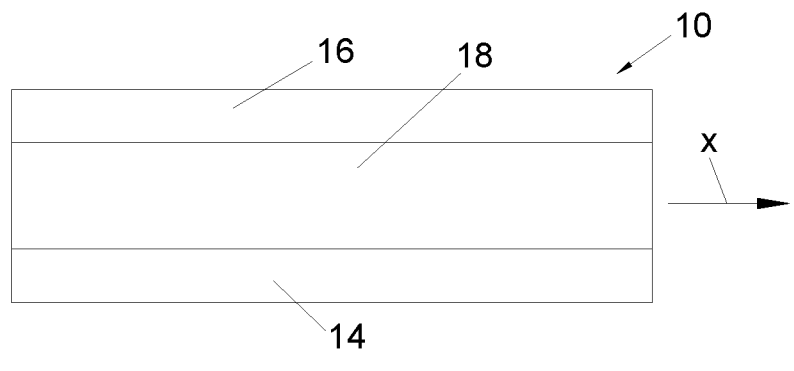

In a second step, shown in FIG. 2, a continuous elastic tape 18 is fed in the same longitudinal direction X and is overlapped to the central portion 12 of the first continuous web 10.

The elastic tape 18 is elastically stretched in a direction Y transversal to the longitudinal direction X when it is applied to the central portion 12 of the continuous web 10. The continuous elastic tape 18 may have the capability to extend in the transversal direction Y by at least 100%, and preferably by 300%, with respect to the rest dimension and to return to the rest dimension in the absence of a transversal force. In a possible embodiment, the degree of transversal elastic stretching of the continuous elastic tape 18 may be in the order of 200%. This means that the continuous elastic tape 18 is applied on the first continuous web 10 with a width essentially equal to three times the width that the continuous elastic tape 18 has at rest, i.e., in the absence of transversal forces.

The transverse extension of the continuous elastic tape 18 may be obtained by a spreading device comprising two wheels with respective axes inclined with respect to each other, as disclosed in EP-A-3213728.

The transversely stretched continuous elastic tape 18, once applied to the respective central portion 12 of the first continuous web 10 may be retained in the stretched state by vacuum suction, as disclosed in EP-A-3213728.

Figure 3:
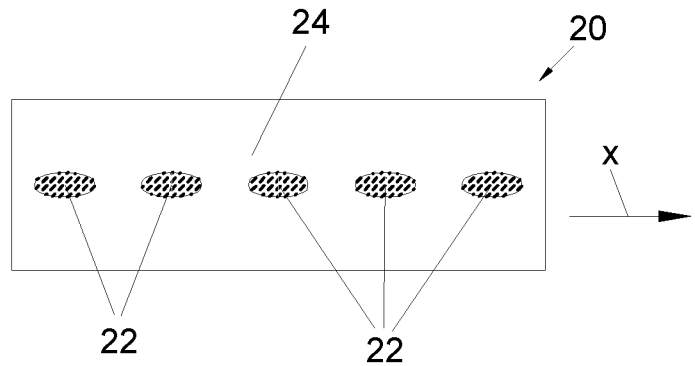

With reference to FIG. 3, the method comprises providing a continuous support web 20 advancing in the longitudinal direction X. A row of micro-hook pads 22 is fixed to a planar surface 24 of the support web 20. The row of micro-hook pads 22 is located in a central portion of the support web 20. The micro-hook pads 22 are spaced apart from each other in the longitudinal direction X. The micro-hook pads 22 may be fixed to the planar surface 24 of the support web 20 by any conventional means, for instance by glue, thermomechanical welding, ultrasonic welding, etc.

In a possible embodiment, the micro-hook pads 22 may have the respective micro-hooks alternately oriented in opposite directions, so that in each pair of adjacent micro-hook pads 22 the micro-hooks of one pad 22 are oriented in a direction opposite with respect to the micro-hooks of the other pad 22.

Figure 4:
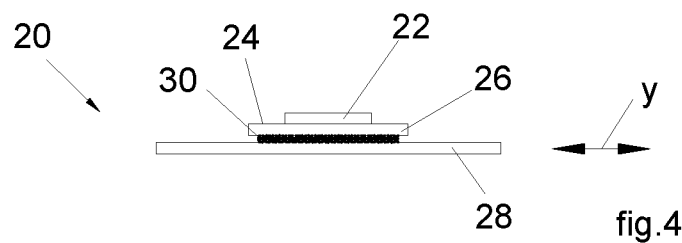
FIG. 4 is a schematic cross-section showing a possible embodiment of a continuous support web used in the method according to the invention.

With reference to FIG. 4, in a possible embodiment the continuous support web 20 may comprise a first layer 26 carrying the row of micro-hook pads 22 and a second layer 28 joined to the first layer 26, for instance by a glue layer 30. In the transversal direction Y the second layer 28 is substantially wider than the first layer 26. The first layer 26 should have a relatively large mechanical resistance for supporting the micro-hook pads whereas the second layer 28 does not need a great mechanical resistance. Both the first layer 26 and the second layer 28 may be made of non-woven materials. This solution allows a reduction of costs, in that the more robust and more expensive first layer 26 may have reduced dimensions (it may have a width only a few millimetres greater than the width of the micro-hook pads 22) whereas the second layer 28 which can be less resistant and less expensive than the first layer 26 has a larger width. The first layer 26 with the micro-hook pads 22 fixed thereto may be manufactured by producers of web materials for absorbent sanitary articles and may be supplied in reels. In the method for producing the transversely extensible continuous elastic laminate according to the present invention, the first layer 26 and the second layer 28 may be unwound from respective reels and may be joined to each other, for instance by the glue layer 30, as they advance in the longitudinal direction X. This has the additional advantage of having reels which are more compact and less subject to damages.

Figure 5:
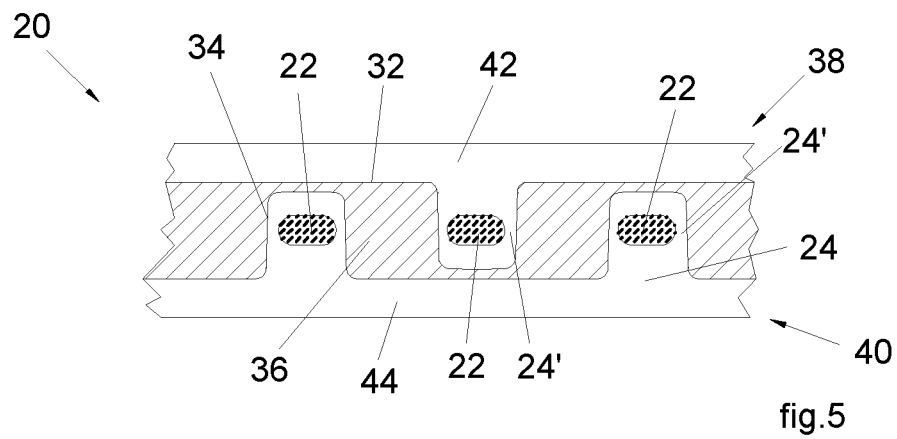

With reference to FIG. 5, the method further comprises a cutting step wherein the continuous support web 20 is cut along two continuous undulated cutting lines 32, 34 passing between each pair of adjacent micro-hook pads 22. The continuous undulated cutting lines 32, 34 may be made by a cutting roller having a shaped cutting blade. The continuous undulated cutting lines 32, 34 are distanced from the edges of the micro-hook pads 22 so that each micro-hook pad 22 is completely surrounded by a portion 24' of the planar surface 24 of the support web 20. The continuous undulated cutting lines 32, 34 may pass at a distance from the edges of said micro-hook pads 22 comprised between 1-10 mm and preferably comprised between 2-7 mm.

The two continuous undulated cutting lines 32, 34 define a continuous undulated strip 36, shown by hatched lines in FIG. 5, comprised between the two cutting lines 32, 34 which is discarded as waste.

Figure 6:
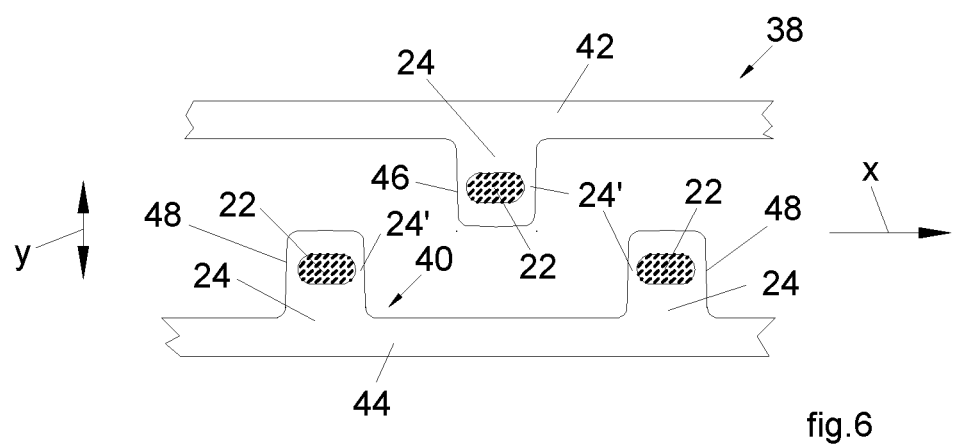

With reference to FIG. 6, after the cut of the support web 20 along the two continuous undulated cutting lines 32, 34 two separate continuous tab chains 38, 40 are formed, which are offset from each other in the longitudinal direction X. The two continuous tab chains 38, 40 comprise respective continuous base portions 42, 44 and respective tabs 46, 48 projecting from the respective continuous base portions 42, 44 in the transversal direction Y. Each tab 46, 48 has a respective micro-hook pad 22 surrounded by a portion 24' of the flat surface 24. In each continuous tab chain 38, 40 the respective tabs 46, 48 are spaced apart from each other in the longitudinal direction X.

Figure 7:
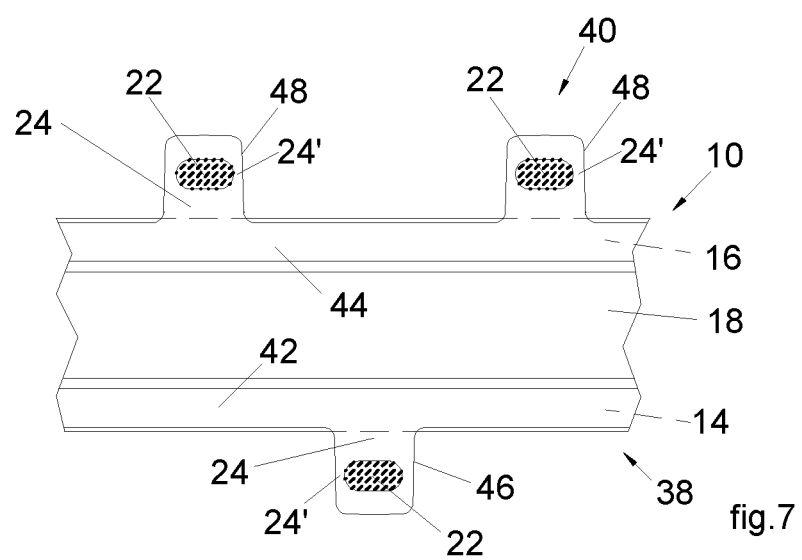

After the cut of the support web 20 along the two continuous undulated cutting lines 32, 34 the two separate continuous tab chains 38, 40 have the respective tabs 46, facing inward with respect to a longitudinal centre line. After the cut, the two separate continuous tab chains 38, 40 are crossed with each other as they advance in the longitudinal direction, in order to bring the two separate continuous tab chains 38, 40 in a position in which the respective tabs 46, 48 face outward with respect to a longitudinal centre line. Then, as shown in FIG. 7, the two continuous base portions 42, 44 of the two continuous tab chains 38, 40 are overlapped, respectively, to the first edge portion 14 and to the second edge portion 16 of the first continuous web 10.

Figure 8:
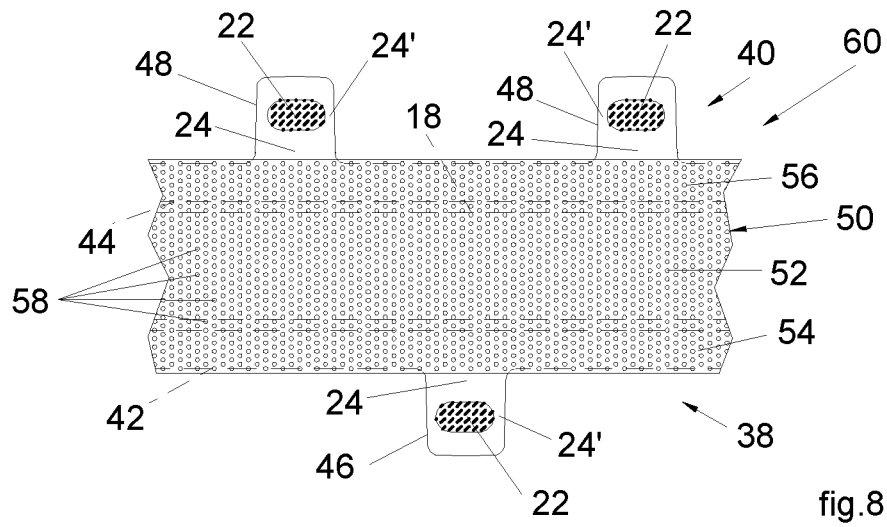

In a further step shown in FIG. 8, a second continuous web 50 is fed in the longitudinal direction X and is overlapped to the first continuous web 10.

The second continuous web 50 may have the same width as the first continuous web 10 and may be made of the same material (e.g. a non-woven material). The second continuous web 50 has a central portion 52 and first and second edge portions 54, 56 opposite to each other with respect to the central portion 12.

The second continuous web 50 is applied over the first continuous web 10 so that the continuous elastic tape 18 is sandwiched between the respective central portions 12, of the first and second webs 10, 50. Also, the two continuous base portions 42, 44 of the two continuous tab chains 38, 40 may be sandwiched between respective first edge portions 14, 54 of the first and second continuous web 10, 50.

Then, the first and second web 10, 50, the elastic tape 18 and the two continuous base portions 42, 44 of the two continuous tab chains 38, 40 are joined to each other by a pattern of spot welds 58. The spot welds 58 may be formed by ultrasonic welding as disclosed in EP-A-3213728. The pattern of spot welds 58 may have a reinforced area along the longitudinal portion connecting the two continuous base portions 42, 44 of the two continuous tab chains 38, 40 to the respective first edge portions 14, 54 and second edge portions 16, 56 of the first and second continuous web 10, 50 in order to provide an increased joining strength in these areas.

The elastic tape 18 is stretched in the transversal direction Y during the spot welding which joins the elastic tape 18 to the first and second web 10, 50. The welding spots 58 may form through holes in the elastic tape 18 in order to provide breathability features to the composite laminate, as disclosed in EP-A-3213728.

After the spot-welding step, a finished transversely extensible continuous elastic laminate 60 is obtained.

The tabs 46, 48 of the two continuous tab chains 38, 40 may be folded over the second web 50 along respective folding lines parallel to the longitudinal axis X, so that the micro-hook pads 22 are releasably fastened to corresponding portions of the second web 50. When the tabs 46, 48 are folded over the second continuous web 50 the transversely extensible continuous elastic laminate 60 can be handled more easily without the risk that the micro-hook pads 22 engage with a non-woven web when the transversely extensible continuous elastic laminate 50 is wound in a reel or during the manufacturing process of absorbent sanitary products.

Figure 9:
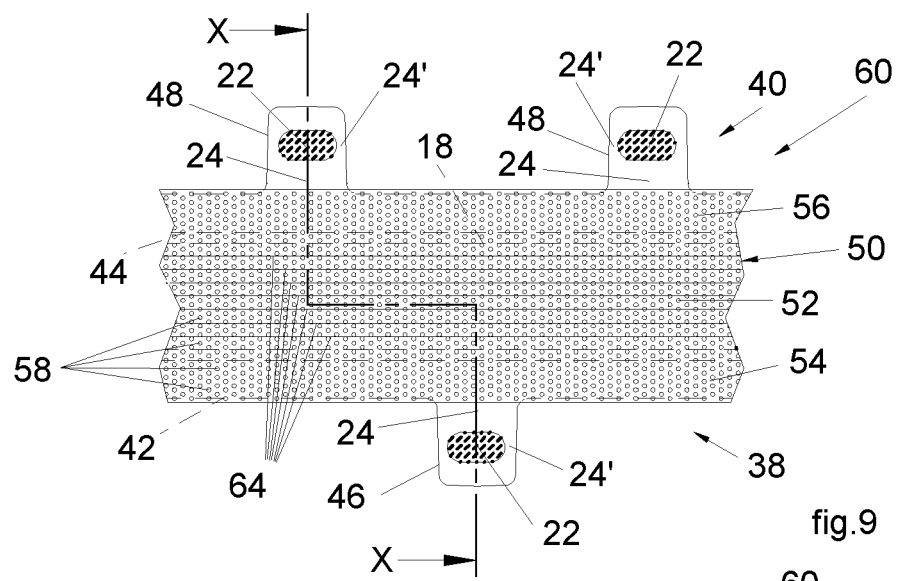
Figure 10:
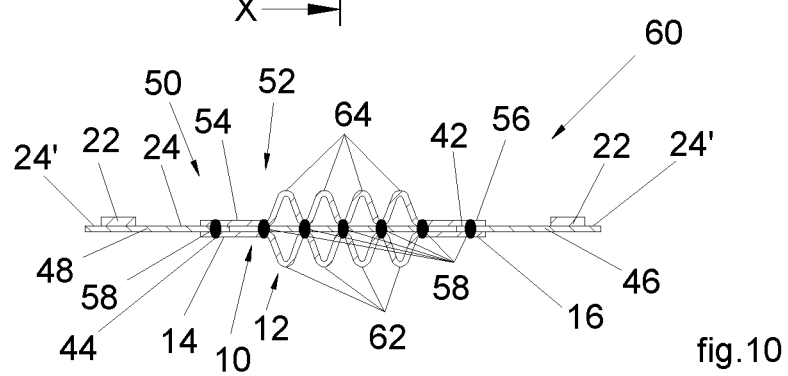
FIG. 10 is a schematic cross-section taken along the line X-X of FIG. 9.

With reference to FIGS. 9 and 10, when the vacuum suction which holds the elastic tape 18 stretched in the transversal direction Y is released, the elastic tape 18 contracts in the transversal direction Y. The transversal contraction of the elastic tape 18 forms longitudinal pleats 62, 64 on the central portions 12, 52 of the first and second continuous web 10, 50. The edge portions 14, 54 and 16, 56 of the first and second continuous webs 10, 50 which extend transversally beyond the elastic tape 18 remain non-pleated.

With reference to FIGS. 9 and 10, the transversely extensible continuous laminate 60 obtained by the previously disclosed method comprises a first and second continuous web 10, 50 overlapped to each other and extending along a longitudinal direction X. The first and second continuous web 10, 50 have respective pleated central portions 12, 52 having longitudinal pleats 62, 64 and respective first and second non-pleated edge portions 14, 54 and 16, 56.

A continuous elastic tape 18 elastically extensible in a transverse direction Y is sandwiched between the pleated central portions 12, 52 of the first and second continuous webs 10, 50 and joined thereto by a pattern of spot welds 58.

The transversely extensible continuous elastic laminate 50 comprises a first and a second continuous tab chain 38, 40, having respective continuous base portions 42, 44 and respective tabs 46, 48 carrying respective micro-hook pads 22 fixed to respective planar surfaces 24 of the tabs 46, 48. The micro-hook pads 22 of each of the tabs 46, 48 is completely surrounded by a portion 24' of the planar surface 24.

In each continuous tab chain 38, 40 the respective tabs 46, 48 are spaced apart from each other in the longitudinal direction X. The tabs 46, 48 of the two continuous tab chains 38, 40 are offset with respect to each other.

The continuous base portions 42, 44 of the first and second continuous tab chain 38, 40, are sandwiched between the respective first and second non-pleated edge portions 14, 54 and 16, 56 of the first and second continuous web 10, 50 and are joined thereto by said pattern of spot welds 58. The pattern of spot welds 58 may be reinforced in the areas connecting the continuous base portions 42, of the first and second continuous tab chain 38, 40, and the respective first and second non-pleated edge portions 14, 54 and 16, 56 of the first and second continuous web 10, 50.

In a possible embodiment the micro-hook pads 22 of the first and second continuous tab chain 38, 40 may have respective hooks oriented in opposite direction to each other.

In a possible embodiment each of the first and second continuous tab chain 38, 40 comprises a first layer 26 forming distal portions of the tabs 46, 48 and carrying the micro-hook pads 22, and a second layer 28 joined to the first layer 26 and forming the continuous base portion 42, 44 and intermediate portions of the tabs 46, 48 extending between the distal portions and the continuous base portion 42, 44. The first layer 26 and second layer 28 may be joined to each other by a glue layer 30.

In a possible embodiment the portion 24' of the planar surface 24 may have a width greater than 2 mm. The width of each tab 46, 48 along a line parallel to the direction X and passing through the respective micro-hook pad 22 should be at least 4 mm larger than the width of the micro-hook pad 20 along the same line (2 mm on each side of the micro-hook pad 20). The width of each tab 58 may be 100 mm larger than the width of the micro-hook pad 20. For instance, if the width of the micro-hook pad 20 is 50 mm, the width of the respective tab 58 may be comprised between 54 mm and 150 mm.

In the finished transversely extensible continuous elastic laminate the tabs 46, 48 of the two continuous tab chains 38, 40 may be folded over the second web 50 along respective folding lines parallel to the longitudinal axis X, so that the micro-hook pads 22 are releasably fastened to corresponding portions of the second web 50.

The transversely extensible continuous elastic laminate 60 shown in FIG. 9 can be wound in reels which can be stored and shipped to manufacturing plants. The reels containing the transversely extensible continuous elastic laminate 60 are intended to produce elastic side panels in machines for manufacturing absorbent sanitary articles.

In a possible embodiment, the transversely extensible continuous elastic laminate 50 may be formed in-line with respect to a manufacturing machine, so that the transversely extensible continuous elastic laminate 60 are supplied in-line to the manufacturing machine without being previously collected in reels.

In a possible embodiment, the method previously disclosed may be carried out using two first continuous webs 10, two continuous elastic tapes 18, two continuous support webs 20 and two second continuous webs 50, advancing along two parallel directions to produce two transversely extensible continuous elastic laminates 60. Each of the parallel pairs of webs or tapes may be obtained from a single continuous web or tape unwound from a single reel and cut longitudinally so as to form two separate webs or tapes advancing parallel to each other in the longitudinal direction X.

Figure 11:
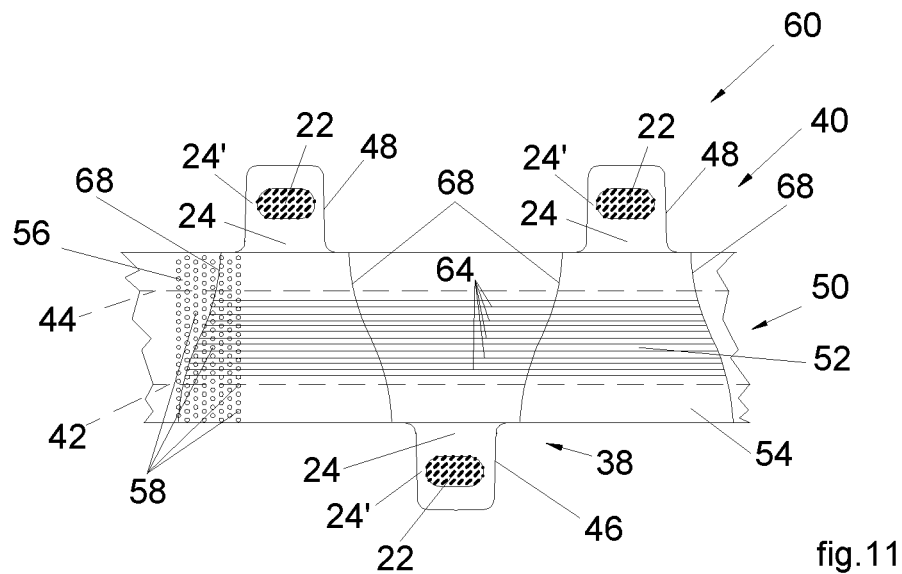
FIG. 11 is a schematic plan view showing a step of cutting the transversely extensible continuous elastic laminate for forming elastic side panels for absorbent sanitary articles.

With reference to FIG. 11, in the machine for manufacturing absorbent sanitary products, the transversely extensible continuous elastic laminate 60 is cut along cutting lines 66 generally transversal to the longitudinal axis X for forming individual elastic side panels. The cutting lines 66 which form the individual elastic side panels may have different shapes so as to form elastic side panels with the desired shape. The cuts which originate the individual elastic side panels are typically carried out while the tabs 46, 48 of the transversely extensible continuous elastic laminate 60 are folded over the second continuous web.

Figure 12:
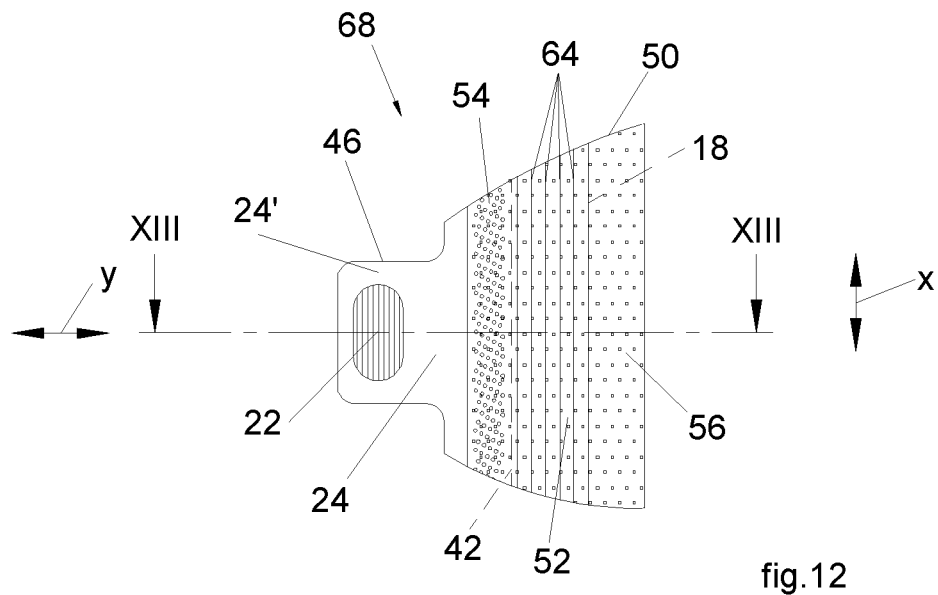
FIG. 12 is a schematic plan view showing an elastic side panels for absorbent sanitary articles.
Figure 13:
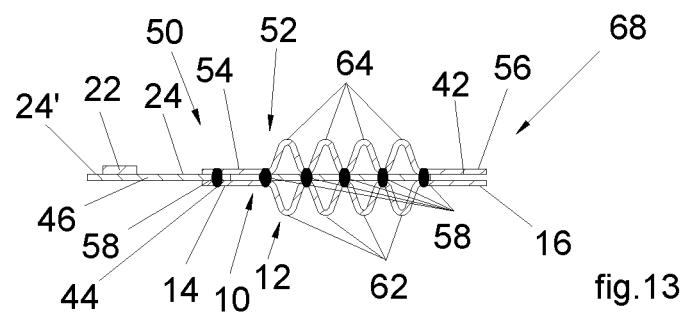
FIG. 13 is a schematic cross-section taken along the line XIII-XIII of FIG. 12.

FIGS. 12 and 13 show an elastic side panel 68 obtained from a transversely extensible continuous elastic laminate 60. The elastic side panel 68 is shown in an extended position for a better understanding.

The elastic side panel 68 comprises a first and a second web 10, 50 having respective pleated central portions 12, 54 having respective pleats 52, 54 parallel to a first direction X, and respective first and second non-pleated edge portions 14, 54 and 16, 56 on opposite sides of the pleated central portions 12, 52. An elastic tape 18 is sandwiched between the pleated central portions 12, 52 of the first and second web 10, 50. The elastic tape 18 is elastically stretchable in a second direction Y transversal to the first direction X. The elastic tape 18 is joined to the first and second web 10, 50 by a pattern of spot welds 58.

The elastic side panel 68 comprises a tab 46 including a base portion 42 sandwiched between the first non-pleated edge portions 14, 54 and fixed thereto by said pattern of spot welds 58. The pattern of spot welds 58 may be reinforced in the area connecting the first non-pleated portions 14, 54 of the first and second web 10, 50 to the base portion 42 of the tab 46. The base portion 42 of the tab 46 in the first direction X has the same length as the non-pleated edge portions 14, 54 of the first and second web 10, 50. The tab 46 has a distal portion extending from the base portion 42 outside the first and second web 10, 50. A micro-hook pad 22 is fixed to a planar surface 24 of the tab 46. The planar surface 24 of the tab 46 has a portion 24' which completely surrounds the micro-hook pad 22. The portion 24' of the planar surface 24 may have a width comprised between 1-10 mm and preferably comprised between 2-7 mm.

In a possible embodiment the tab 46 may comprise a first layer 26 forming a distal portion of the tab 46 and carrying the micro-hook pad 22, and a second layer 28 joined to the first layer 26 and forming the base portion 42 and an intermediate portion of the tab 46 extending between said distal portion and the base portion 42.

An absorbent sanitary article may have an absorbent central body and two or four elastic side panels 68 as previously described fixed to two opposite longitudinal edges of said central body.

As compared to the prior art disclosed in EP-A-3213728, the elastic side panel 68 according to the present invention has an increased resistance and is less exposed to the risk of breaks because the tab 46 is connected to the webs 10, 50 along the whole length of the webs 10, 50.

In use, the tabs 68 have a soft feeling to the touch because the rigid and sharp micro-hook pads 22 are completely surrounded by the web material of the tab 46. In use the user never touches the sharp edges of the micro-hook pads 22 and does not run the risk of getting skin scratches against the sharp edges of the micro-hook pads 22.

The method for manufacturing the transversely extensible continuous elastic laminate 60 does not require the application of discrete tabs on the edges of the elastic laminate. The tabs 46, 48 with the respective micro-hook pads 22 are formed by applying and cutting a continuous web. This involves considerable advantages in that there is no need for complex and expensive repitch devices for applying discrete elements at a constant pitch.

Of course, without prejudice to the principle of the invention, the details of construction and the embodiments can be varied, even significantly, with respect to those illustrated here without departing from the scope of the invention as defined by the following claims.

This applies, in particular but not exclusively, to the possibility to vary as desired the shape of the micro-hook pads 22 and to the choice of the materials forming the webs. For instance, one or more of the webs 10, 50, 26, 28 may be formed by a film of plastic material (such as polythene).

The invention claimed is:

1. A transversely extensible continuous elastic laminate comprising:
    first and second continuous webs extending along a longitudinal direction, having respective pleated central portions having pleats parallel to said longitudinal direction and respective first and second non-pleated edge portions on opposite sides of said pleated central portions,
    a continuous elastic tape extending in said longitudinal direction, and sandwiched between said pleated central portions of said first and second webs, wherein said elastic tape is elastically stretchable in a direction transversal to said longitudinal direction, and wherein said elastic tape is joined to the first and second webs by a pattern of spot welds,
    first and second continuous tab chains having respective continuous base portions sandwiched between respective first and second non-pleated edge portions of the first and second webs and fixed thereto by said pattern of spot welds, and respective tabs extending from the respective base portions outside said first and second webs and carrying respective micro-hook pads fixed to respective planar surfaces of said tabs, said respective tabs of each tab chain being connected to each other by said respective continuous base portions, wherein said micro-hook pads are completely surrounded by respective portions of said planar surface.

2. The transversely extensible continuous elastic laminate of claim 1, wherein in each of said continuous tab chains the respective tabs are spaced apart from each other in said longitudinal direction and wherein the tabs of the two continuous tab chains are offset with respect to each other.

3. The transversely extensible continuous elastic laminate of claim 1, wherein said tabs are folded over one of said first and second webs along folding lines parallel to said first direction and said micro-hook pads are releasably fastened to corresponding portions of the one of said first and second web.

4. The transversely extensible continuous elastic laminate of claim 1, wherein the micro-hook pads of said first and second continuous tab chains have respective hooks oriented in opposite direction to each other.

5. The transversely extensible continuous elastic laminate of claim 1, wherein each of said first and second continuous tab chains comprises a first layer forming distal portions of said tabs and carrying said micro-hook pads, and a second layer joined to the first layer and forming said continuous base portion and intermediate portions of said tabs extending between said distal portion and said continuous base portion.

6. An elastic side panel for absorbent sanitary articles, comprising:
   first and second webs, having respective pleated central portions having pleats parallel to a first direction, and respective first and second non-pleated edge portions on opposite sides of said pleated central portions,
   an elastic tape sandwiched between said pleated central portions of said first and second webs, wherein said elastic tape is elastically stretchable in a second direction transversal to said first direction, wherein said elastic tape is joined to the first and second webs by a pattern of spot welds,
   a tab including a base portion sandwiched between said non-pleated edge portions of said first and second webs and fixed thereto by said pattern of spot welds, said base portion having in said first direction the same length as said non-pleated edge portions, the tab extending from the base portion outside said first and second webs and having a micro-hook pad fixed to a planar surface of the tab, wherein said planar surface of said tab has a portion which completely surrounds the micro-hook pad.

7. The elastic side panel of claim 5, wherein said tab is folded over one of said first and second webs along a folding line parallel to said first direction and said micro-hook pad is releasably fastened to a corresponding portion of the one of said first and second webs.

8. The elastic side panel of claim 6, wherein said tab comprises a first layer forming a distal portion of the tab and carrying said micro-hook pad, and a second layer joined to the first layer and forming said base portion and an intermediate portion of said tab extending between said distal portion and said base portion.

9. A method for producing the continuous transversely extensible elastic laminate according to claim 1 comprising:
   feeding a first continuous web in a longitudinal direction, the first continuous web having a central portion and first and second edge portions on opposite sides of the central portion,
   feeding a continuous elastic tape in said longitudinal direction,
   elastically stretching said continuous elastic tape in a direction transversal to said longitudinal direction, and applying said continuous elastic tape to the central portion of said first continuous web while stretched in said transversal direction,
   feeding in said longitudinal direction, a continuous support web having a row of micro-hook pads fixed to a planar surface of the support web, wherein said micro-hook pads are spaced apart from each other in said longitudinal direction,
   cutting the continuous support web along two continuous undulated cutting lines passing between each pair of adjacent micro-hook pads so as to form two separate continuous tab chains having respective continuous base portions and respective tabs carrying respective micro-hook pads fixed to respective planar surfaces of said tabs, wherein said cutting lines are distanced from edges of the micro-hook pads, so that each micro-hook pad is completely surrounded by a portion of said planar surface,
   applying said two continuous base portions of said continuous tab chains to respective first edge portions of said first continuous web,
   feeding a second continuous web in said longitudinal direction, the second continuous web having a central portion and first and second edge portions on opposite sides of the central portion,
   applying said second continuous web to the first continuous web and sandwiching said continuous elastic tape between respective central portions of said first and second webs, and said two continuous base portions of said continuous tab chains between respective first and second edge portions of the first and second continuous webs, and
   joining to each other said first and second webs, said elastic tape and said two continuous base portions of said continuous tab chains by a pattern of spot welds.

10. The method of claim 9, wherein in each of said continuous tab chains the respective tabs are spaced apart from each other in said longitudinal direction and wherein the two continuous tab chains are applied to the first web so that the tabs of the two continuous tab chains are offset with respect to each other.

11. The method of claim 9, wherein the micro-hook pads of said first and second continuous tab chains have respective micro-hooks oriented in opposite direction to each other.

12. The method of claim 9, wherein said tabs are folded over one of said first and second webs along folding lines parallel to said first direction and said micro-hook pads are releasably fastened to corresponding portions of one of said first and second webs.

13. The method of claim 9, wherein said continuous support web is formed by:
   unwinding from a first reel a first layer having a row of micro-hook pads applied thereon,
   unwinding from a second reel a second layer having a width in said transversal direction substantially larger than a width of said first layer, and
   joining to each other said first layer and second layer.

14. A method for producing elastic side panels for absorbent sanitary articles, comprising producing a continuous transversely extensible elastic laminate by the method according to claim 9, and cutting the continuous transversely extensible elastic laminate along cutting lines to form individual elastic side panels.

* * * * *

UNITED STATES PATENT AND TRADEMARK OFFICE
CERTIFICATE OF CORRECTION

| | | |
|---|---|---|
| PATENT NO. | : 11,903,800 B2 | Page 1 of 1 |
| APPLICATION NO. | : 17/675306 | |
| DATED | : February 20, 2024 | |
| INVENTOR(S) | : Guido Bonelli and Gabriele Sablone | |

It is certified that error appears in the above-identified patent and that said Letters Patent is hereby corrected as shown below:

On the Title Page

(71) Applicant address information should be listed as:
- Fameccanica.Data S.p.A., San Giovanni Teatino (Chieti), ITALY -

(72) Inventor address information should be listed as:
- Guido BONELLI, San Giovanni Teatino (Chieti), ITALY
  Gabriele SABLONE, San Giovanni Teatino (Chieti), ITALY -

Signed and Sealed this
Eleventh Day of March, 2025

Coke Morgan Stewart
*Acting Director of the United States Patent and Trademark Office*